United States Patent
Cho et al.

(10) Patent No.: US 10,011,882 B2
(45) Date of Patent: Jul. 3, 2018

(54) PHOTO-RESPONSIVE COMPOSITE ACTUATOR

(71) Applicant: Seoul National University R&DB Foundation, Seoul (KR)

(72) Inventors: Maeng Hyo Cho, Seoul (KR); Joon Myung Choi, Seongnam-si (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 15/612,451

(22) Filed: Jun. 2, 2017

(65) Prior Publication Data

US 2017/0349956 A1    Dec. 7, 2017

(30) Foreign Application Priority Data

Jun. 3, 2016    (KR) .................... 10-2016-0069599

(51) Int. Cl.
| | | |
|---|---|---|
| *C08F 4/04* | (2006.01) | |
| *C08F 20/60* | (2006.01) | |
| *C12Q 1/6888* | (2018.01) | |
| *A61F 2/02* | (2006.01) | |
| *B25J 9/10* | (2006.01) | |

(52) U.S. Cl.
CPC .............. *C12Q 1/6888* (2013.01); *A61F 2/02* (2013.01); *B25J 9/1095* (2013.01)

(58) Field of Classification Search
CPC ......... C12Q 1/6888; B25J 9/1095; A61F 2/02
USPC ................................................ 526/218.1, 307
See application file for complete search history.

(56) References Cited

U.S. PATENT DOCUMENTS

| | | | | |
|---|---|---|---|---|
| 8,901,247 | B2 * | 12/2014 | Lu ..................... | B82Y 30/00 |
| | | | | 525/418 |
| 2010/0052196 | A1 * | 3/2010 | Yasuda .............. | C07C 245/08 |
| | | | | 264/1.34 |

FOREIGN PATENT DOCUMENTS

| | | |
|---|---|---|
| JP | 3137275 B2 | 2/2001 |
| JP | 2007-106945 A | 4/2007 |
| JP | 5224261 B2 | 7/2013 |
| KR | 20130011880 A | 1/2013 |
| KR | 20160017278 A | 2/2016 |

OTHER PUBLICATIONS

Office Action issued in corresponding Korean Application No. 10-2016-0069599 dated Aug. 15, 2017 (5 pages).

* cited by examiner

*Primary Examiner* — William K Cheung
(74) *Attorney, Agent, or Firm* — Osha Liang LLP

(57) ABSTRACT

A photo-responsive composite actuator according to the present invention includes a polymeric scaffold film; an azobenzene liquid crystal polymer applied on a surface of the polymeric scaffold film; and a protective film attached to a surface of the azobenzene liquid crystal polymer.

7 Claims, 5 Drawing Sheets

PHOTO-RESPONSIVE COMPOSITE ACTUATOR

CROSS-REFERENCE TO RELATED APPLICATION

This application claims priority to and the benefit of Korean Patent Application No. 2016-0069599, filed on Jun. 3, 2016, the disclosure of which is incorporated herein by reference in its entirety.

BACKGROUND

1. Field of the Invention

The present invention relates to a composite actuator, and particularly, to a photo-responsive composite actuator capable of controlling bending deformation by light radiation.

2. Discussion of Related Art

Recently, a great deal of research for applying intelligent composite actuators which exhibit mechanical responses by external stimuli to actively or manually control a structure has been conducted.

An intelligent composite actuator generally uses an intelligent material such as a shape-memory alloy, a piezoelectric material and an electro-active polymer, and may be used in the form of a driver by directly attaching such an intelligent material to a structure or by inserting such an intelligent material into other materials.

In Korean Patent Application Publication No. 10-2013-0011880, one example of an intelligent composite actuator is disclosed. The composite actuator disclosed in the document includes an intelligent material whose shape can be deformed due to an external signal such as a current signal and a directional material which can support the intelligent material, regulate an exterior shape, and suppress deformation in a specific direction, and realizes the deformation of the composite actuator by a combination of the arrangement form of the intelligent material and the deformation suppressing directivity of the directional material.

In addition, in Korean Patent Application Publication No. 10-2016-0017278, another example of an intelligent composite is disclosed. The composite actuator disclosed in the document realizes the deformation thereof using a wire instead of an intelligent material. As a wire is pulled by an external force, the composite actuator is bent or twisted.

In this way, known composite actuators need to supply heat or electric energy to generate heat energy in a material, or provide direct mechanical tension in order to cause deformation.

Meanwhile, a great deal of research on the design of an intelligent composite actuator using an azobenzene liquid crystal polymer has been progressing recently.

Azobenzene is composed of two benzene ring linked by a N=N double bond, and has a unique property in which two different geometric forms are interconverted by light. Benzene rings linked on both sides based on the N=N double bond of azobenzene are linked by a single bond that is able to freely rotate. A case where benzene rings at both ends of the N=N double bond are positioned on the same side is referred to as a cis form, and a case where benzene rings are positioned on opposing sides is referred to as a trans form. Azobenzene undergoes photo-isomerization in which the molecular structure thereof is converted from a trans form to a cis form upon irradiation with UV rays, and the molecular structure thereof is converted from a cis form to a trans form upon irradiation with visible rays.

An azobenzene liquid crystal polymer is an azobenzene-based liquid crystal polymer including azobenzene or an azobenzene derivative (hereinafter, referred to as "azobenzene"), and has a photo-reactive behavior characteristic due to photo-isomerization of azobenzene. When a liquid crystal polymer with azobenzene in a trans form is irradiated with UV rays, azobenzene is isomerized, and thus nematic-isotropic phase transition characteristics of an adjacent liquid crystal polymer are induced, thereby bending deformation in which a polymer material is bent in a direction of receiving light occurs. Also, the photo-reactive deformation of such an azobenzene liquid crystal polymer, which is a reversible reaction, is known to return to an original form upon irradiation with visible rays.

Recently, research on the manufacture of an actuator such as a photo-reactive actuator or the like using photo-reactive deformation characteristics of such an azobenzene liquid crystal polymer has been actively progressing, and in order to utilize these photo-reactive deformation characteristics of the azobenzene liquid crystal polymer, it is necessary to determine the directivity of photo-deformation through alignment.

Therefore, recently, research on various methods for simplifying the alignment of an azobenzene liquid crystal polymer has been conducted.

SUMMARY OF THE INVENTION

The present invention is directed to providing a photo-responsive composite actuator which is capable of controlling bending deformation using cis-trans conversion of an azobenzene liquid crystal polymer.

The present invention is directed to providing a photo-responsive composite actuator prepared without an alignment process by coating a surface of a polymeric scaffold film with an azobenzene liquid crystal polymer.

A photo-responsive composite actuator according to the present invention includes a polymeric scaffold film; an azobenzene liquid crystal polymer applied on a surface of the polymeric scaffold film by immersing the film in the polymer; and a protective film attached to a surface of the azobenzene liquid crystal polymer.

According to the present invention, the polymeric scaffold film may have a porous structure. Preferably, the porous structure may be formed by intertwining polymer fibers constituting the polymeric scaffold film and having pores. More preferably, the polymeric scaffold film may have a mesh structure.

According to the present invention, the azobenzene liquid crystal polymer may be applied on both surfaces of the polymeric scaffold film.

According to the present invention, the polymeric scaffold film may have a concave pattern.

According to the present invention, the protective film may have a pattern composed of a light transmission portion configured to transmit ultraviolet (UV) rays and a light-blocking portion configured to suppress UV transmission, contrary to the light transmission portion.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, a photo-responsive composite actuator according to an embodiment of the present invention will be described in detail with reference to the accompanying drawings.

Figure 1:
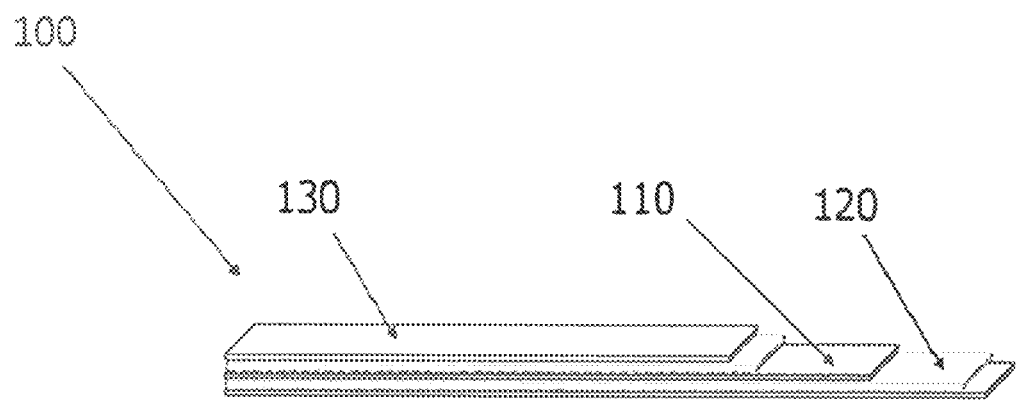
FIG. 1 is a diagram illustrating a structure of a photo-responsive composite actuator according to an embodiment of the present invention.

FIG. 1 is a diagram illustrating a structure of a photo-responsive composite actuator according to an embodiment of the present invention.

A composite actuator 100 according to the present invention includes a polymeric scaffold film 110, an azobenzene liquid crystal polymer 120 applied on a surface of the polymeric scaffold film 110 by immersing the film in the polymer, and a protective film 130 attached to a surface of the azobenzene liquid crystal polymer 120.

The azobenzene liquid crystal polymer 120 is an azobenzene-based liquid crystal polymer, and various azobenzene-based liquid crystal polymers including azobenzene and an azobenzene derivative may be used.

The azobenzene liquid crystal polymer 120 is applied on the polymeric scaffold film 110. The coating is performed by a method in which a dissolved liquid azobenzene liquid crystal polymer is applied on a surface of the polymeric scaffold film or the polymeric scaffold film 110 is immersed in a dissolved liquid azobenzene liquid crystal polymer to impregnate a surface of the polymeric scaffold film 110 with the azobenzene liquid crystal polymer.

According to an embodiment illustrated in FIG. 1, the azobenzene liquid crystal polymer is applied on both surfaces of the polymeric scaffold film, but may be applied on only one surface according to bending behavior characteristics required in another embodiment.

The polymeric scaffold film 110 is a polymeric scaffold prepared in a film form. As the polymeric scaffold film 110, various materials such as poly(lactic acid) (PLA), poly(D,L-lactic-co-glycolic acid) (PLGA), poly(dimethylsiloxane) (PDMS), polycaprolactone (PCL) and the like may be used.

The polymeric scaffold is, for example, a two-dimensional weaving material with a ribbon or mesh structure prepared by spinning and discharging a polymer fiber having a μm- or nm-scale diameter onto a dust-collecting plate through an electrospinning process. However, the polymeric scaffold film according to the present invention is not limited to a specific processing method or a micro structure. The polymeric scaffold may be fabricated, for example, through a micromolding process and a spincoating process for forming a polymer matrix with a μm-scale porous pattern or a microsyringe deposition method in which a polymer in a gel state is put into a syringe and then a two-dimensional pattern is drawn through a micro-needle located at an outermost edge of the syringe.

In an embodiment of the present invention, the polymeric scaffold film may be in the form of a two-dimensional film having a very thin thickness compared to a width and a length, preferably, major axis slenderness ratio with respect to a thickness of 1:10000 or more. Such a polymeric scaffold film is distinguished from a polymeric scaffold as a three-dimensional porous support which is mainly applied in tissue engineering and biomedical engineering.

According to the present invention, the polymeric scaffold film 110 preferably has a porous micro-structural pattern with pores between fibers by intertwining polymer fibers of which a polymeric scaffold film is formed, and more preferably has a micro-structural pattern with a mesh structure.

The azobenzene liquid crystal polymer 120 is applied on the polymeric scaffold film by permeating the polymer into a pattern in the film.

The protective film 130 is attached to a surface of the azobenzene liquid crystal polymer 120. The protective film 130 supports a composite actuator so that a fracture does not occur even at high tension, and a flexible material which does not degrade the bending deformation of a composite actuator is used as the protective film.

When a position where bending is required in the composite actuator 100 thus manufactured is irradiated with UV rays using a UV laser or UV LED, a surface which is irradiated with UV rays is locally contracted, and thus bending deformation occurs throughout the composite actuator. A direction in which bending deformation occurs may be an upper surface or lower surface of the composite actuator 100 according to a direction in which light is radiated, but, according to the present invention, the deformation characteristics of the composite actuator 100 are not related to an alignment direction of azobenzene molecules in the azobenzene liquid crystal polymer applied on the polymeric scaffold film. That is, according to the present invention, the azobenzene liquid crystal polymer 120 does not require separate alignment in addition to being applied on the polymeric scaffold film 110.

Based on research conducted by a researcher of the present invention, it was confirmed that, when a liquid azobenzene liquid crystal polymer is applied on a surface of the polymeric scaffold film 110 and dried or a surface of a polymeric scaffold film is immersed in an azobenzene liquid crystal polymer, that is, the polymeric scaffold film 110 is impregnated with a liquid azobenzene liquid crystal polymer and dried, the azobenzene liquid crystal polymer may have regular deformation characteristics in which bending behavior is exhibited in a direction in which UV rays are radiated without alignment of the azobenzene liquid crystal polymer 120 in a specific direction. Therefore, active control is possible according to the light irradiation position, intensity, and time designated by a user. In addition, when a composite actuator which exhibits bending behavior is irradiated with visible rays, the composite actuator returns to an original form.

According to the present invention, a photo-responsive composite actuator 100 with a simpler structure may be manufactured through a simpler process. According to the present invention, when a small amount of the azobenzene liquid crystal polymer 120 is applied on a surface of the polymeric scaffold film 110, photo-deformation behavior characteristics may be effectively exhibited.

According to an embodiment illustrated in FIG. 1, the protective film 130 may generally be a transparent film. However, as described below, according to an embodiment of the present invention, the protective film 130 may be prepared to have a pattern composed of a light transmission portion 132 and a light-blocking portion 134 in order to control the bending behavior of the composite actuator 100. That is, a pattern may be designed by forming the light transmission portion 132 at a position where bending deformation is required and the light-blocking portion 134 at a position where bending deformation is not or relatively less required so that other types of deformation behavior occur.

A method of manufacturing the photo-responsive composite actuator 100 according to an embodiment of the present invention illustrated in FIG. 1 is described as follows.

A powder-type azobenzene liquid crystal polymer 120 was heated, melted, and mixed with a curing agent to apply a liquid azobenzene liquid crystal polymer 120 on both surfaces of a polymeric scaffold film 110. Afterward, the liquid azobenzene liquid crystal polymer 120 was dried at high temperature to form an azobenzene liquid crystal polymer coating layer, and then the protective film 130 was attached thereto. The azobenzene liquid crystal polymer 120 was heated and melted at a temperature of about 80° C., polymerization using a thermal initiator was performed at a high temperature of about 110° C., and then the resulting polymer was dried at room temperature.

Figure 2:
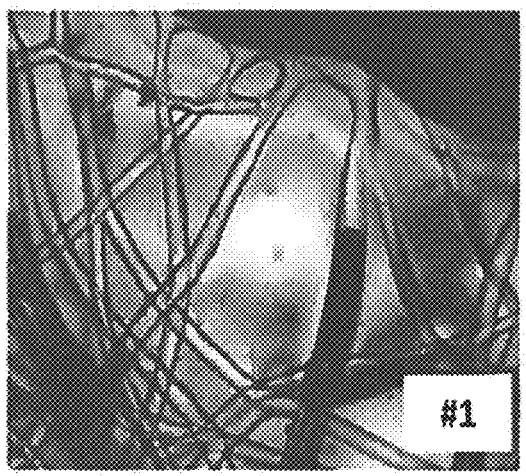
FIG. 2 is a diagram illustrating the observation results of a sample surface of a composite actuator according to the present invention using a polarization microscope.
Figure 2:
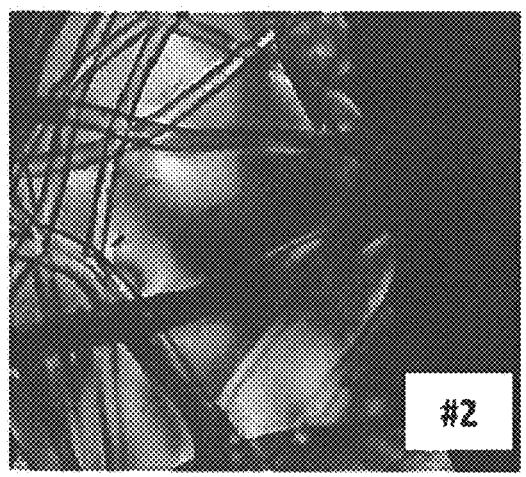
Figure 2:
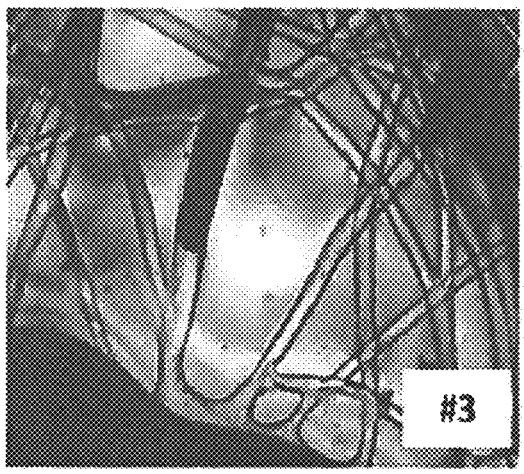
Figure 2:
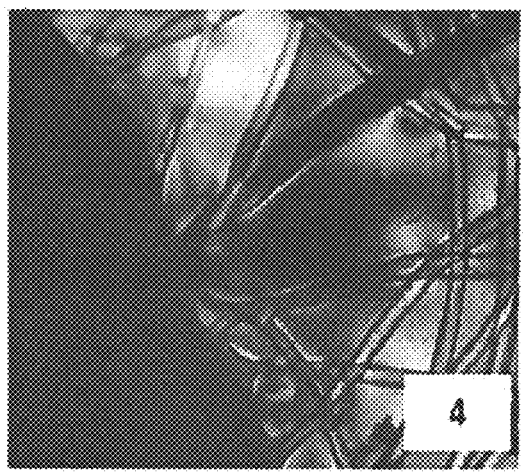

FIG. 2 is a diagram illustrating the observation results of a sample surface of the composite actuator 100 according to the present invention using a polarization microscope. As an azobenzene liquid crystal polymer, a polymer prepared by mixing 6-[4-(4-ethoxyphenylazo)phenoxy]hexyl acrylate and 4,4'-di(6-(acryloxy)hexyloxy)azobenzene, which are commercially available from Beam Co., at a molar ratio of 1:1 and performing polymerization using a thermal initiator was used. As a polymeric scaffold film, poly(lactic acid) (PCL) prepared through an electrospinning process to have a thickness of about 170 μm was used, and a PET film having a thickness of 20 μM was used as a protective film on both surfaces of the actuator.

Referring to FIG. 2, it was confirmed that, when the manufactured product was observed using a polarization microscope, as a sample thereof rotates 45°, an azobenzene liquid crystal polymer filled in an inner space of a scaffold film alternately exhibits a plus and minus pattern, indicating that an azobenzene liquid crystal polymer forms a nematic alignment according to a porous pattern of a scaffold. More specifically, it can be confirmed that, when the nematic alignment of azobenzene formed in a scaffold with a mesh structure is aligned with a polarizing plate of a polarization microscope (see #1 of FIG. 2), it has the brightest color, and, when a sample rotates in a clockwise direction so that an angle formed by the polarizing plate is 45° (see #2 of FIG. 2), an area with the brightest color at the same position changes to the darkest color, and simultaneously a surrounding area with dark color changes to a relatively bright color. The same change in the plus and minus pattern was also exhibited when a sample was photographed under the condition of rotating 180° (#3 and #4 of FIG. 2 indicates that the samples were rotated 180° and 225°, respectively, from the condition of #1 and then were photographed). Based on this experiment, it was confirmed that, in the photo-responsive composite actuator according to the present invention, a nematic liquid crystal alignment in a scaffold occurs despite no separate alignment process.

Therefore, the composite actuator according to the present invention may exhibit a photo-reactive behavior in which bending deformation occurs in a direction in which UV rays are radiated upon irradiation with UV rays even without an alignment of azobenzene in the azobenzene liquid crystal polymer in a specific direction.

Figure 3:
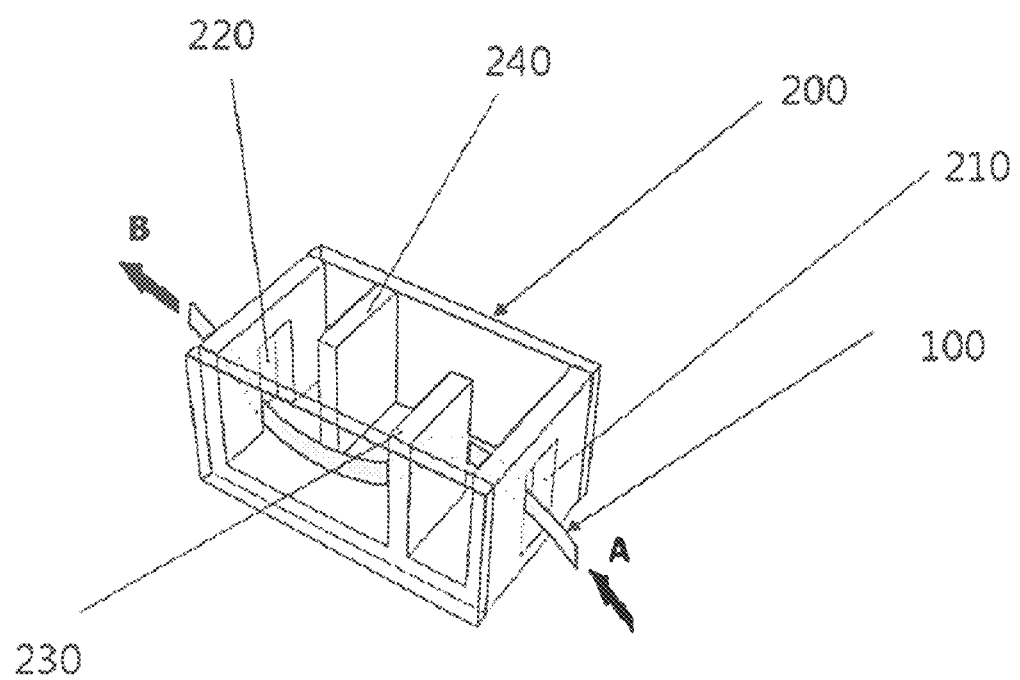
FIG. 3 is a diagram illustrating that a photo-responsive composite actuator according to the present invention passes through an experimental box through photo-reactive driving of the actuator.
Figure 4:
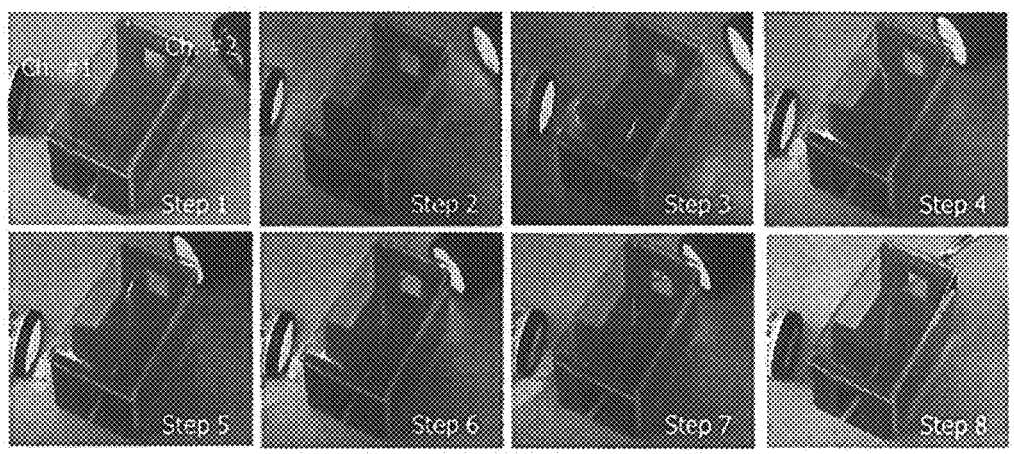
FIG. 4 shows images sequentially illustrating an experimental process in which a composite actuator according to the present invention passes through an experimental box shown in FIG. 3.

FIGS. 3 and 4 are diagrams illustrating actions of the composite actuator 100 according to the present invention. In the composite actuator 100 according to the present invention, bending behavior caused by UV rays may be controlled. That is, in the composite actuator 100 according to the present invention, when UV rays are radiated so that bending deformation occurs at a desired position and a desired level, bending behavior occurs at a desired position and a desired level.

FIG. 3 is a diagram illustrating that the composite actuator 100 according to the present invention passes through an experimental box 200 having first and second obstacles 230 and 240 in a form of a wall disposed in a zigzag form therein so that a straight path between an entrance 210 in one side and an exit 220 in the other side is blocked. FIG. 4 shows images sequentially illustrating a process in which the composite actuator 100 according to the present invention passes through the experimental box shown in FIG. 3. Also, FIG. 5 shows diagrams graphically illustrating a process of step 1 to step 8 shown in FIG. 4.

Figure 5:
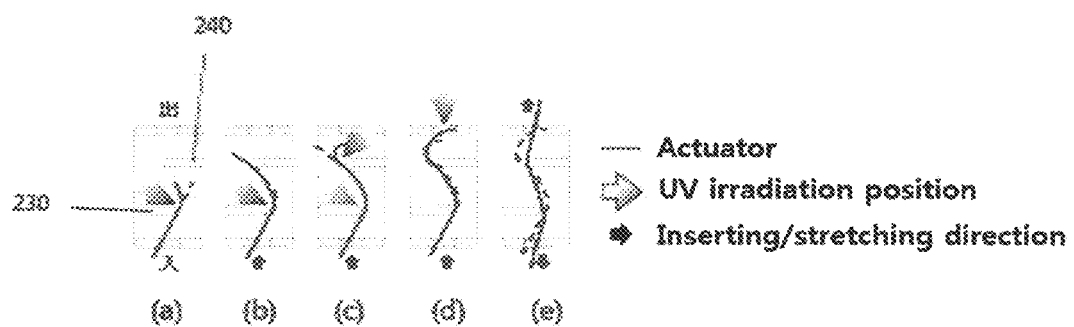
FIG. 5 shows diagrams graphically illustrating an experimental process shown in FIG. 4.

Referring to FIGS. 3 to 5, first, the composite actuator 100 is inserted through the entrance 210 in one side of the experimental box 200 ((A) of FIG. 5). When the composite actuator enters while a left surface of the composite actuator 100 is irradiated with UV rays from the left rear of the first obstacle 230 (an exit direction) using a UV light source in a state in which the composite actuator 100 has passed the first obstacle 230, bending deformation occurs in a left direction so that the composite actuator 100 bypasses the first obstacle 230, and the composite actuator may be continuously inserted toward a space between the second obstacle 240 and an inner side of the experimental box ((B) of FIG. 5).

In addition, when a right surface of the composite actuator 100 is irradiated with UV rays from the rear of the second obstacle 240 using the UV light source in a state in which the composite actuator 100 has passed the second obstacle 240, bending deformation occurs in a right direction so that the composite actuator 100 bypasses the second obstacle 240, and the composite actuator may be continuously inserted ((C) of FIG. 5).

Afterward, when a leading end of the composite actuator 100 enters so as to be adjacent to the exit 220 in the other side of the experimental box 200, a left surface of the composite actuator 100 is irradiated with UV rays from the exit 220 using the UV light source ((D) of FIG. 5). Accordingly, the bending deformation of the composite actuator 100 occurs in a left direction, and the composite actuator may be discharged through the exit 220 ((E) of FIG. 5).

After the composite actuator 100 evades and escapes the obstacles 230 and 240 in the experimental box 200 and thus is physically threaded through the entrance 210 and the exit 220, the composite actuator 100 is not damaged even in an environment in which tension is applied to the composite actuator 100, that is, has durability due to the protective film 230.

Through this process, the composite actuator 100 may bypass and pass the first and second obstacles 230 and 230 between the entrance 210 in one side and the exit 220 in the other side while deformed in a zigzag form.

This experiment shows that, in the composite actuator 100 according to the present invention, a direction of bending behavior and a degree of bending deformation may be controlled by radiating UV rays so that bending deformation occurs at a desired position and a desired level.

Meanwhile, in the experiment illustrated in FIG. 4, a UV LED was used as a UV light source. The composite actuator 100 was irradiated with LED UV light from the outside of the experimental box through a side transparent wall of the experimental box and an opened exit in the other side.

An experiment illustrated in FIG. 4 shows that the composite actuator 100 installed in a closed space in a disconnected state from the outside may be drive-controlled using light in remote locations. Therefore, the photo-responsive composite actuator 100 according to the present invention may be deformed in a desired form if UV rays can be provided although it is installed in a space that is disconnected from the outside or cannot be accessed by a person.

Figure 6:
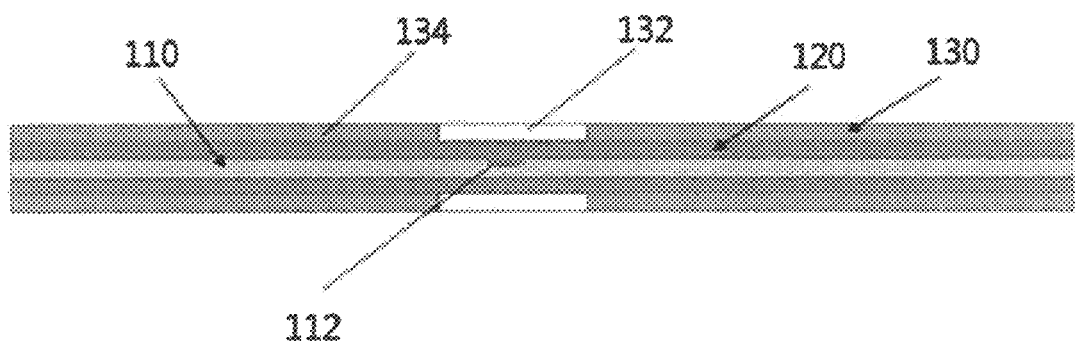
FIG. 6 is a side sectional view of a photo-responsive composite actuator according to another embodiment of the present invention.

FIG. 6 is a side sectional view of a photo-responsive composite actuator 100 according to another embodiment of the present invention.

According to another embodiment of the present invention, the polymeric scaffold film 110 includes a concave portion 112 in the form of a groove extending in a transverse direction crossing the lengthwise direction on one side surface, compared to the polymeric scaffold film of the composite actuator illustrated in FIG. 1.

Also, the azobenzene liquid crystal polymer 120 is applied on both surfaces of the polymeric scaffold film 110, and the protective film 130 is attached to both outer surfaces of the composite actuator.

According to an embodiment illustrated in FIG. 6, when one surface of the composite actuator 100 is irradiated with UV rays, the concave portion 112 of the polymeric scaffold film 110 acts as a kind of a hinge portion, and thus the composite actuator may be controlled to exhibit relatively large bending behavior. That is, a composite actuator which exhibits a partially different degree of bending deformation may be manufactured by forming a constant concave pattern for constant bending behavior of the polymeric scaffold film 110 in addition to a method of adjusting an amount of UV irradiation. In an embodiment illustrated in FIG. 6, only the polymeric scaffold film 110 having the concave portion pattern is illustrated, but the present invention is not limited thereto, and various shapes of a film and a pattern may be applied.

In addition, referring to FIG. 6, the protective film 130 is designed to have a pattern composed of the transparent light transmission portion 132 configured to transmit ultraviolet (UV) rays in the vicinity of the concave portion 112 requiring bending behavior and the light-blocking portion 134 configured to block UV rays in a portion requiring no bending behavior. Accordingly, bending behavior is suppressed in a portion corresponding to the light-blocking portion 134 of the protective film.

According to the experimental example illustrated in FIGS. 3 to 5, the position requiring bending behavior is irradiated with UV rays. However, as in an embodiment illustrated in FIG. 6, it can be seen that, when the protective film 130 includes the light transmission portion 132 and the light-blocking portion 134, and bending behavior is performed in the composite actuator 100 installed at a fixed position, bending deformation may also be controlled by a method in which UV rays are emitted toward the entire composite actuator 100 rather than a method in which UV rays are emitted toward a specific position.

Figure 7:
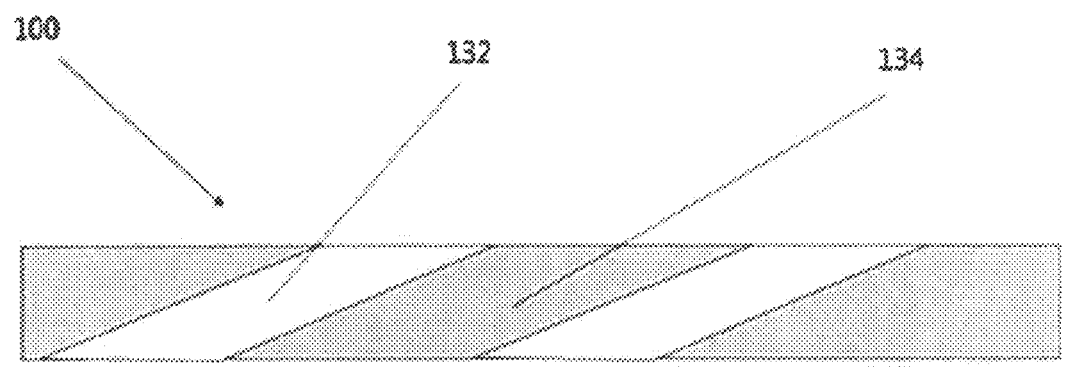
FIG. 7 is a diagram of a surface of a composite actuator according to still another embodiment of the present invention as viewed from above.

FIG. 7 is a diagram illustrating the composite actuator according to still another embodiment of the present invention. Referring to FIG. 7, in the protective film 130, the light transmission portions 132 are formed in a direction crossing the lengthwise direction of the composite actuator in a diagonal form at a constant interval, and the light-blocking portion 134 is formed between the light transmission portions 132. Therefore, when UV rays are radiated, UV rays are transmitted through the light transmission portion 132, and thus an azobenzene liquid crystal polymer undergoes isomerization from a trans form to a cis form to cause bending behavior, thereby the composite actuator 100 may exhibit twisting behavior. Here, the light-blocking portion 134 may not completely block UV rays but may be configured to relatively reduce UV transmittance compared to the light transmission portion 132.

As such, the composite actuator 100 according to the present invention exhibits bending behavior caused by UV radiation, and may realize deformation behavior in various forms as well as bending behavior according to the design of a pattern formed in a polymeric scaffold film and a light transmission pattern of the protective film.

The composite actuator according to the present invention may be applied to design an operating portion of a flexible robot structure which is handled in mm- to cm-scale, and also applied as a mechanical element which controls fluid flow by varying the shape of a film and peripheral equipment. In addition, the composite actuator may be applied in various portions requiring driving control by light in remote locations.

The present invention can provide a photo-reactive composite, which is a composite actuator to which an azobenzene liquid crystal polymer that may be deformed by light is applied and can exhibit photo-reactive behavior by performing an alignment process of azobenzene. Accordingly, a manufacturing method and a structure thereof are simple.

A composite actuator according to the present invention is a composite actuator, which exhibits bending behavior depending on a direction in which UV rays are radiated without alignment of azobenzene molecules and has an advantage in which active control is possible according to the light radiation position, intensity, and time designated by a user.

What is claimed is:

1. A photo-responsive composite actuator comprising:
  a polymeric scaffold film;
  an azobenzene liquid crystal polymer applied on a surface of the polymeric scaffold film by immersing the film in the polymer; and
  a protective film attached to a surface of the azobenzene liquid crystal polymer.

2. The photo-responsive composite actuator according to claim 1, wherein the polymeric scaffold film has a porous structure.

3. The photo-responsive composite actuator according to claim 2, wherein the porous structure of the polymeric scaffold film is formed by intertwining polymer fibers constituting the polymeric scaffold film and having pores.

4. The photo-responsive composite actuator according to claim 3, wherein the polymeric scaffold film has a mesh structure.

5. The photo-responsive composite actuator according to claim 1, wherein the azobenzene liquid crystal polymer is applied on both surfaces of the polymeric scaffold film.

6. The photo-responsive composite actuator according to claim 1, wherein the polymeric scaffold film has a concave pattern.

7. The photo-responsive composite actuator according to claim 1, wherein the protective film has a pattern composed of a light transmission portion configured to transmit ultraviolet (UV) rays and a light-blocking portion configured to suppress UV transmission, contrary to the light transmission portion.

\* \* \* \* \*